(12) United States Patent
Stockmans et al.

(10) Patent No.: US 12,138,173 B2
(45) Date of Patent: *Nov. 12, 2024

(54) HEMI ARTHROPLASTY JOINT IMPLANT

(71) Applicant: Loci Orthopaedics Limited, Galway (IE)

(72) Inventors: Filip Stockmans, Heule Kortrijk (BE); Gerry Clarke, County Galway (IE); Arnold-Peter C. Weiss, Barrington, RI (US); Amy L. Ladd, Stanford, CA (US); Brendan Boland, County Kildare (IE)

(73) Assignee: Loci Orthopaedics Limited, Galway (IE)

( * ) Notice: Subject to any disclaimer, the term of this patent is extended or adjusted under 35 U.S.C. 154(b) by 526 days.

This patent is subject to a terminal disclaimer.

(21) Appl. No.: 17/442,736

(22) PCT Filed: Feb. 28, 2020

(86) PCT No.: PCT/EP2020/055353
§ 371 (c)(1),
(2) Date: Sep. 24, 2021

(87) PCT Pub. No.: WO2020/193079
PCT Pub. Date: Oct. 1, 2020

(65) Prior Publication Data
US 2022/0218492 A1    Jul. 14, 2022

Related U.S. Application Data

(60) Provisional application No. 62/847,710, filed on May 14, 2019, provisional application No. 62/823,392, (Continued)

(51) Int. Cl.
*A61F 2/42* (2006.01)
*A61F 2/30* (2006.01)

(52) U.S. Cl.
CPC .......... *A61F 2/4241* (2013.01); *A61F 2/4261* (2013.01); *A61F 2002/3006* (2013.01); (Continued)

(58) Field of Classification Search
CPC .................. A61F 2/4241; A61F 2/4261; A61F 2002/4258; A61F 2002/30614; A61F 2002/30607; A61F 2002/30616
See application file for complete search history.

(56) References Cited

U.S. PATENT DOCUMENTS

| | | | |
|---|---|---|---|
| 9,078,758 B2 * | 7/2015 | Leibel | A61F 2/4261 |
| 10,799,365 B1 * | 10/2020 | Stockmans | A61F 2/4241 |
| 11,213,401 B2 * | 1/2022 | Clarke | A61F 2/30 |
| 11,712,340 B2 * | 8/2023 | Stockmans | A61F 2/4261 623/21.13 |

(Continued)

FOREIGN PATENT DOCUMENTS

| | | | | |
|---|---|---|---|---|
| EP | 1402854 A2 | 3/2004 | | |
| FR | 2805151 A1 * | 8/2001 | ........... | A61F 2/4241 |
| WO | WO-2007056678 A3 * | 3/2008 | ............... | A61F 2/32 |

(Continued)

OTHER PUBLICATIONS

International Search Report in International Application No. PCT/EP2020/055353, mailed May 13, 2020 (6 pages).

*Primary Examiner* — Alvin J Stewart
(74) *Attorney, Agent, or Firm* — Bookoff McAndrews, PLLC

(57) ABSTRACT

A hemi-arthroplasty bone joint implant has a first part (120) with a stem (111) tor intramedullary implanting into a metacarpal, and a second part (110) to engage the trapezium is a translational manner, a hemi-arthroplasty articulating coupling (121). This allows multi-axial motion with translational movement of the second part over the trapezium and rotation of the first part (110) about the articulating coupling (Continued)

(121, 103). There is also a converter to convert the implant to a toral arthroplasty implant in situ during revision surgery. The second part (110) and the hemi-arthroplasty coupling (100, 123, 121) are removable in situ during revision surgery. The first part (120) has an engagement threaded socket (117) for, after removal of the second part and the hemi-arthroplasty coupling, engaging the replacement coupling (200) and allowing mutual articulation of the first (120) and replacement parts (220). This forms a total arthroplasty joint implant.

27 Claims, 9 Drawing Sheets

Related U.S. Application Data filed on Mar. 25, 2019, provisional application No. 62/823,367, filed on Mar. 25, 2019.

(52) U.S. Cl.
CPC ............... *A61F 2002/30663* (2013.01); *A61F 2002/30685* (2013.01); *A61F 2002/30935* (2013.01); *A61F 2002/4258* (2013.01)

(56) References Cited

U.S. PATENT DOCUMENTS

| | | |
|---|---|---|
| 2013/0150975 A1 | 6/2013 | Iannotti et al. |
| 2017/0224499 A1 | 8/2017 | Clarke et al. |
| 2018/0214276 A1 | 8/2018 | Humphrey |

FOREIGN PATENT DOCUMENTS

| | | | | |
|---|---|---|---|---|
| WO | WO-2008095869 A1 | * | 8/2008 | ........... A61F 2/4241 |
| WO | WO-2020193079 A1 | * | 10/2020 | ........... A61F 2/4241 |

* cited by examiner

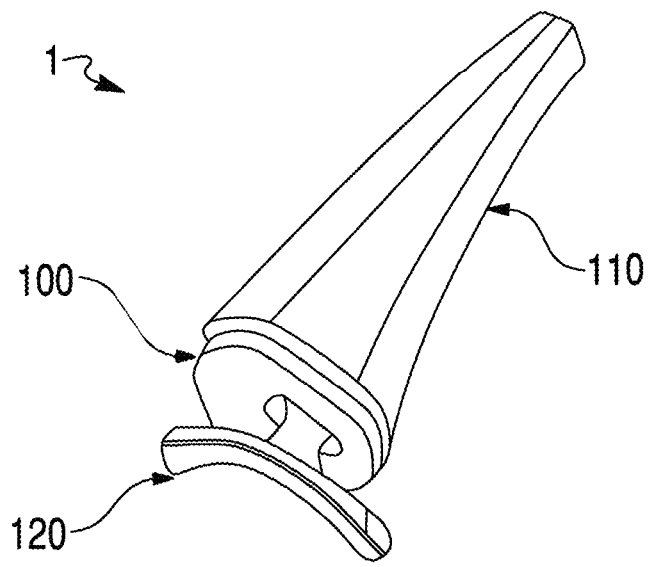
Fig.4
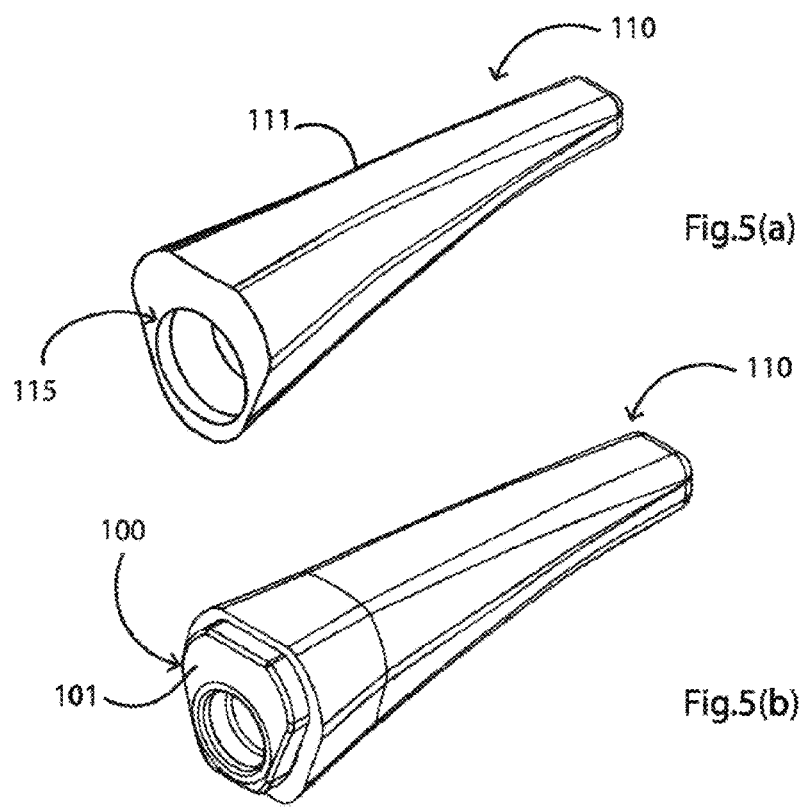
Fig.5(a)
Fig.5(b)

HEMI ARTHROPLASTY JOINT IMPLANT

CROSS REFERENCE TO EARLIER APPLICATIONS

This application is a US National Stage filing under 35 U.S.C. § 371 of International Application No. PCT/EP2020/055353, filed on Feb. 28, 2020, which claims the benefit of priority of U.S. Provisional Application No. 62/847,710 filed on May 14, 2019, and is a continuation-in-part of U.S. patent application Ser. No. 16/678,552 filed on Nov. 8, 2019, which claims the benefit of priority of U.S. Provisional Application Nos. 62/823,367 and 62/823,392, both filed on Mar. 25, 2019, all of which are incorporated herein by reference in their entireties.

INTRODUCTION

The invention relates to a hemi arthroplasty joint implant.

Hemi arthroplasty implants replace a portion of a joint, for example, one articular surface. An example is where one element replaces the metacarpal articular surface and is housed in the metacarpal (FIG. 1), while the other articular surface of the joint does not have an implant component. Hemi arthroplasty implants do not form a linkage across the joint.

On the other hand, total arthroplasty implants are implanted across the joint. An example is a hip implant, where one element is housed in the femur, while another is housed in the acetabulum of the pelvis. These parts are linked across the joint, providing a "total" replacement of joint function.

For a mammalian first carpometacarpal ("CMC") joint it will be noted that the hemi arthroplasty implants (FIGS. 1 and 2) are not linked across the joint by attachment in the trapezium bone. FIG. 3 illustrate that for a total arthroplasty an implant has a part housed in the metacarpal and another in the trapezium, with a linkage across the joint.

If a surgeon was to choose to change from a hemi arthroplasty device to a total arthroplasty device, this would require the initial removal of the hemiarthroplasty implant. However, removal of an implant which has been in place for some time can be technically and clinically challenging. It may result in significant bone loss, which in turn may prohibit the use of a total arthroplasty due to insufficient bone stock.

The invention addresses this problem.

SUMMARY OF THE INVENTION

We describe a bone joint implant as set out in any of appended claims 1 to 23, and kit of an implant and converters as set out in appended claim 24 or 25, and a method of performing revision surgery as set out in appended claim 26 or 27.

We describe a hemi-arthroplasty bone joint implant comprising:
  a first part configured to be implanted into bone,
  a second part configured to engage bone is a translational manner, and
  a hemi-arthroplasty articulating coupling between the first and second parts, wherein the implant is configured for multi-axial motion with translational movement of the second part over a bone and rotation of the first part about the articulating coupling.

The second part and the hemi-arthroplasty coupling are removable in situ during revision surgery. The first part comprises an engagement feature for engaging a replacement coupling replacing the hemi arthroplasty coupling, whereby a replacement implantable part can engage the replacement coupling and so replace the second part for mutual articulation of the first and replacement parts as a total arthroplasty joint implant.

Preferably, the engagement feature comprises a bolt or threaded socket aligned for positioning of a replacement coupling for conversion to a total arthroplasty joint implant.

Preferably, the engagement feature comprises a threaded socket, and said threaded socket is at an angle relative to the first part for optimum positioning of a replacement coupling with respect to an axis of the first part.

Preferably, the threaded socket opens into a socket in the first part, a liner is removably insertable into said socket of the first part, whereby the threaded socket is exposed after said removal.

Preferably, the liner is configured to limit relative rotational motion about the hemi-arthroplasty coupling, and to provide resilience for contact between the first and second parts; and wherein the liner comprises a flange extending radially and around at least some of the hemi-arthroplasty coupling, and wherein the flange is of material which is more resilient than material which it contacts.

Preferably, the flange has a contoured surface matching an abutting surface of the second part upon articulation of the parts in use to extreme positions, and wherein the flange contoured surface is annular.

Preferably, the flange has a thickness in the range of 0.5 mm and 4.0 mm, preferably in the range of 1.0 mm and 3 mm; and wherein the flange is of a material which is non-metal and is different from the material of a contacting surface.

Preferably, the flange is configured to provide a cone of motion in the range of 30° and 50° of the first part about the second part.

Preferably, the hemi-arthroplasty coupling is a ball-and-socket coupling and the liner includes the socket of the coupling and a lock feature for snap-fitting into the first part.

Preferably, the implant is for a mammalian first carpometacarpal joint, and the second part is configured for translational motion on the trapezium bone and the first part is configured for intramedullary engagement with an end of the first metacarpal bone.

We also describe a converter for in situ conversion of any hemi arthroplasty bone joint implant described herein to a total arthroplasty bone joint implant during revision surgery, the converter comprising:
  a replacement implantable part, and
  a replacement coupling arranged to engage on one side with the engagement feature of the first part and to engage with the replacement implantable part on the other side.

Preferably, the replacement coupling comprises a stem with a threaded distal end and a ball forming a proximal end.

Preferably, the replacement coupling comprises an enlarged portion to fit within a socket of the first part with engagement of at least some surfaces.

Preferably, the replacement coupling comprises an integral nut for fastening the replacement coupling to the first part.

Preferably, the replacement coupling comprises a neck supporting a ball which is tilted at an angle to a longitudinal axis of the coupling.

Preferably, the replacement coupling has a threaded end for engaging the first part engagement feature, whereby extent of rotation to a final position determines an angle of tilt of the neck and the ball.

Preferably, the replacement implantable part comprises a cup to receive a ball.

Preferably, the replacement implantable part further comprises a cup liner to directly receive a ball of the replacement coupling.

Preferably, the first part comprises an intra medullary stem for implanting in a bone.

We also describe a kit comprising:
any hemi arthroplasty bone joint implant as described herein, and
any converter described herein.

We also describe a method of converting any hemi arthroplasty implant described herein to a total arthroplasty implant using any converter described herein, the method comprising, in a revision surgery, removing the second part and the articulating coupling, and implanting the replacement implantable part in a bone and connecting it to the first part with the replacement coupling.

In one example, the hemi arthroplasty implant is across a mammalian first carpometacarpal joint, with the second part arranged for translational motion on the trapezium bone and the first part is engaged within an end of the first metacarpal bone.

DETAILED DESCRIPTION OF THE INVENTION

The invention will be more clearly understood from the following description of some embodiments thereof, given by way of example only with reference to the accompanying drawings in which:

FIG. 4 is an image showing in perspective an implant, both proximal and distal parts;

FIG. 5(a) is a perspective view of the stem of the distal part, FIG. 5(b) is a perspective view of the complete distal part.

Figure 8:
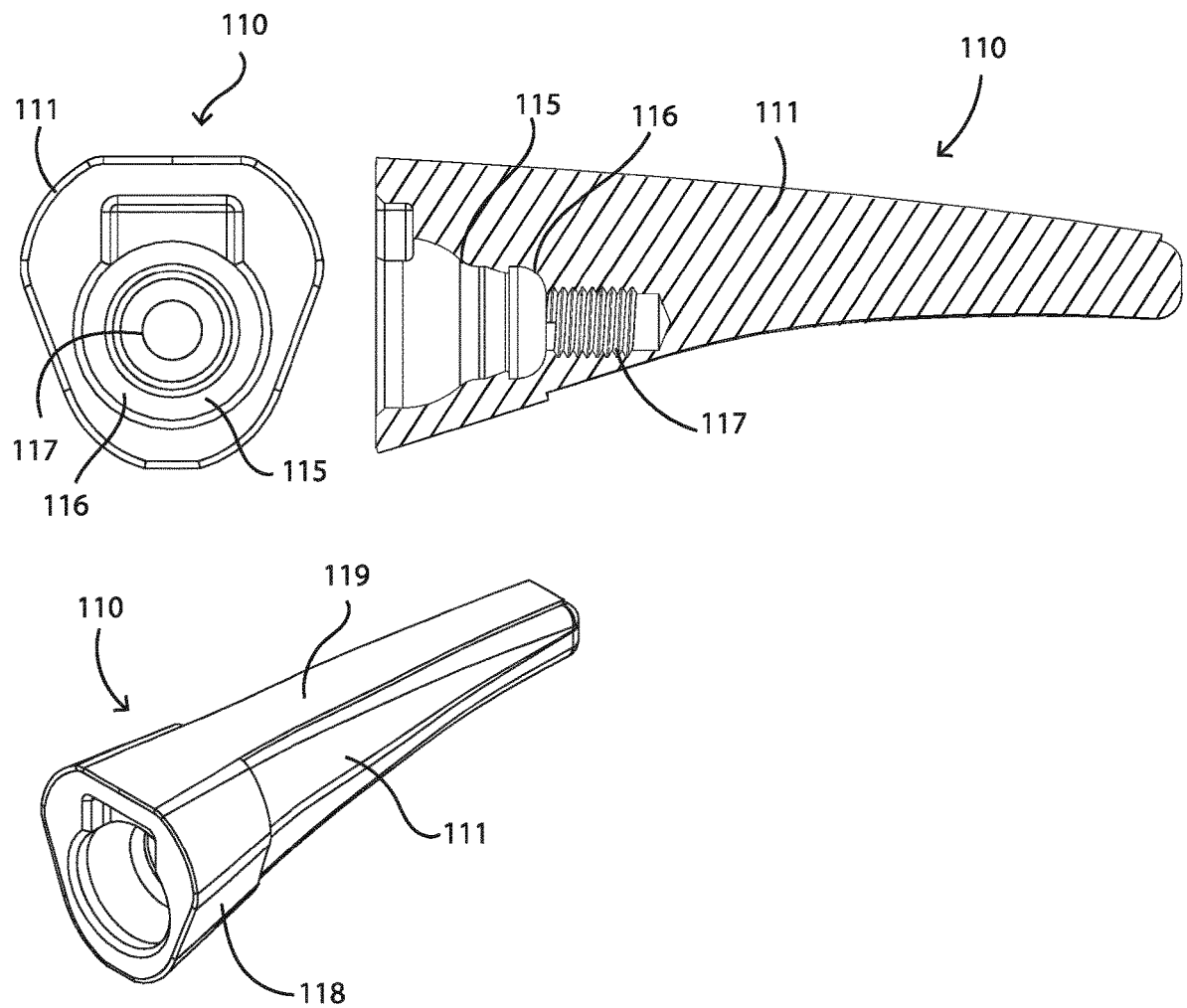
Figure 10:
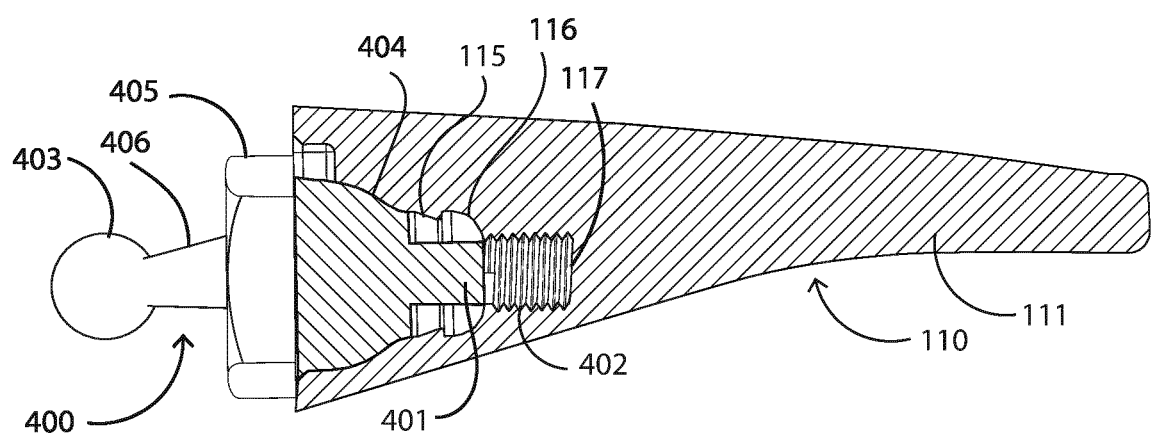
Figure 11A:
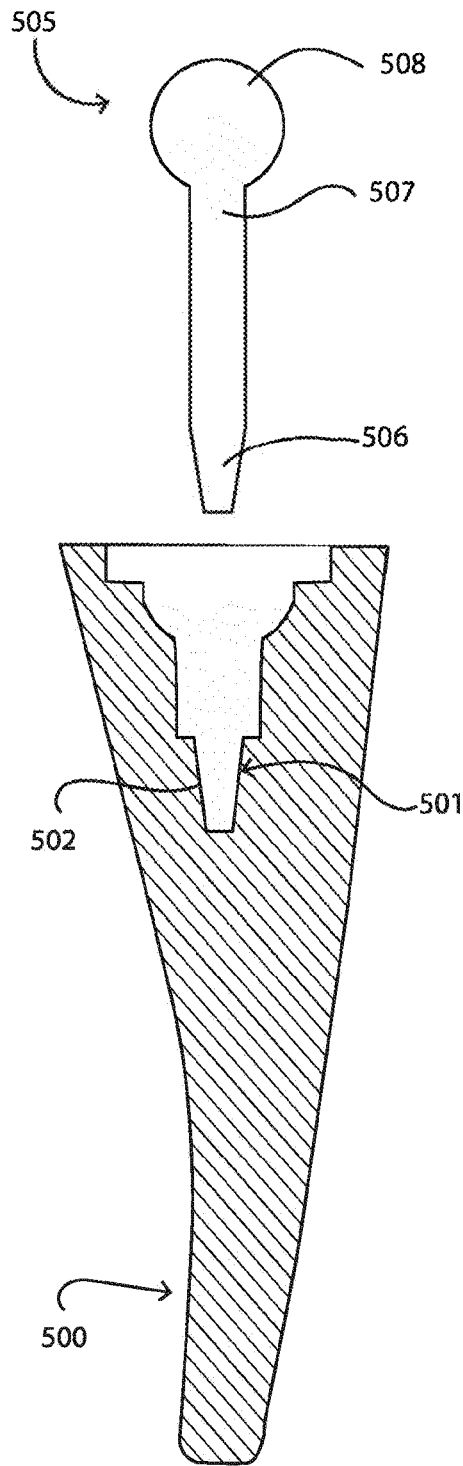
Figures 12A, 12B:
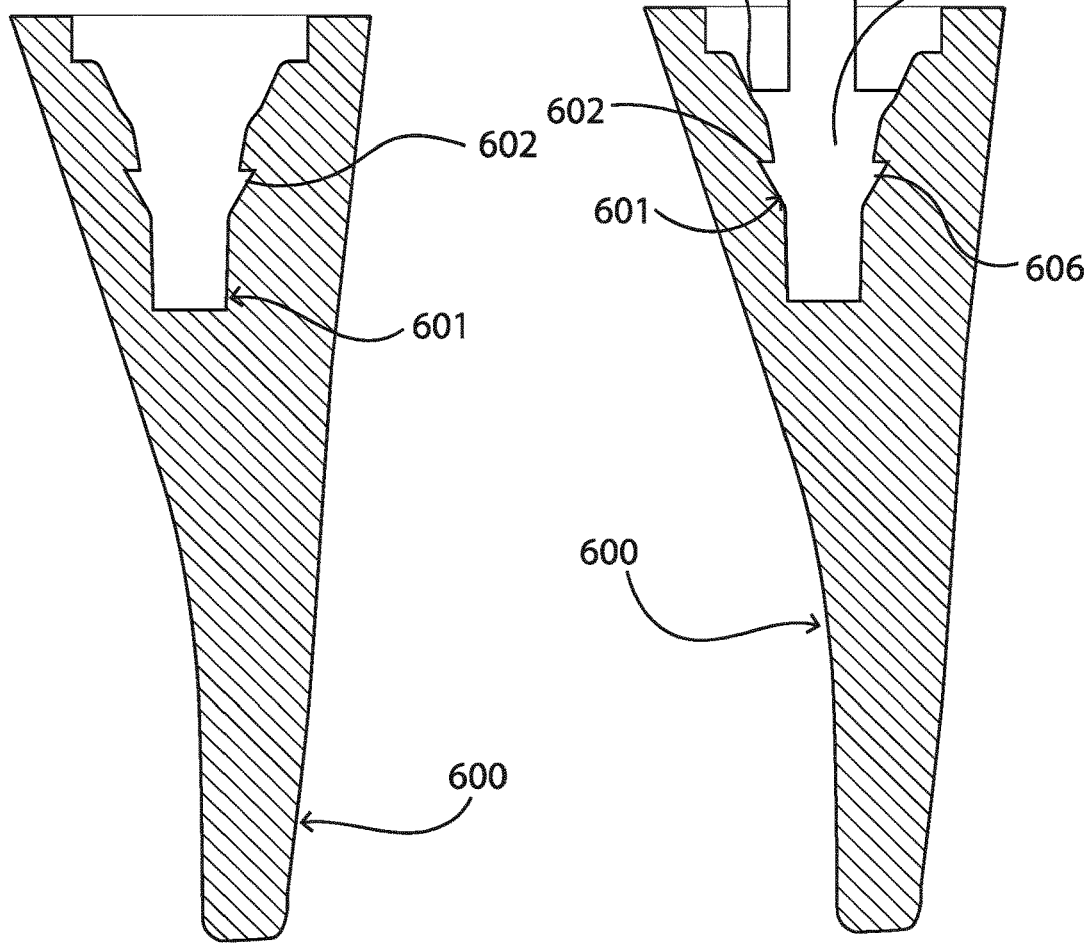

FIGS. 7(a), 7(b), and 7(c) are a set of views of the hemiarthroplasty implant in use;

FIG. 8 is a cross-sectional view, an end view, and a perspective view of the stem part of the implant;

FIGS. 9(a), 9(b) and 9(c) are diagrammatic sectional views illustrating conversion of the implant to a total arthroplasty implant;

FIG. 10 is a side view of an alternative implant after conversion, with the stem and parts within it in cross-section and those outside it (on the left) being in side view;

FIGS. 11(a) and (b) are diagrams illustrating insertion of replacement coupling into a distal part intramedullary stem, in which the engagement is by way of Morse taper; and FIGS. 12(a) and 12(b) are diagram showing insertion of a replacement coupling into a distal part intramedullary stem, in which the engagement is by way of a snap fit.

TERMS

"Intramedullary engagement" means engagement within a medullary cavity formed or existing in the bone, where the cavity is generally but not exclusively formed along a longitudinal axis of the bone. In one embodiment, the intramedullary engagement fixture comprises a screw or nail or interference-fit stem, although other intramedullary fixtures are known. Typically, the screw is externally threaded.

"Non-engaging abutment" means that the proximal part is not fixed to the first bone, but is configured to abut the end of the bone in a manner that allows translational movement thereof. How this is achieved depends on the joint being treated and the specific anatomy of the first bone. As an example, when the joint is a carpometacarpal joint in the thumb, the end of the trapezium bone has a twisted saddle shape (see FIG. 2 of Turker et al, Indian J Plast Surg. 2011, 44(2): 308-316) and the platform is configured to rest upon this saddle and allow translational movement of the platform across the saddle.

"Translational movement" means non-pivoting movement, which can also be described as sliding movement. An example is the involuntary translational movement of the metacarpal in relation to the trapezium in the thumb carpometacarpal joint, which contributes significantly to extension-flexion articulation of the thumb.

"Articulating coupling" means a coupling that allows articulation between the first and second parts of the implant. The specific type of coupling employed in the implant depends on the joint that is being treated with the implant, and in some cases the indication or severity of the indication. For example, when the implant is for treatment of an arthritic hinge joint, for example an elbow joint, the implant will generally comprise a hinge joint coupling. When the implant is for treatment of a saddle joint, for example a carpometacarpal joint, the implant will generally comprise a ball and socket joint or a universal joint. "Controlled articulation" means that the articulation is constrained to specific types of articulation.

"Abutting platform" means a base that abuts the end of the first bone (for example the end of the trapezium) so that translational (i.e. sliding) movement of the platform in relation to the end of the bone is allowed. The bone is not fixed to the platform. The platform may be configured to conform to a surface of the top of the bone. In one embodiment, the platform is shaped to mimic an end of the second bone, so as to allow the same range of movements as the natural healthy joint, including translational movement. In the case of the carpometacarpal joint, where the end of the first bone (trapezium) has a twisted saddle topography, the platform may be shaped to conform to the twisted saddle to allow one or more or all of the following range of movements of the first metacarpal in relation to the trapezium; flexion, extension, abduction, adduction, internal rotation, external rotation, opposition, circumduction and translation.

Description of the Embodiments

Construction and Normal use of the Hemi Arthroplasty Implant (FIGS. 4 to 8)

Figure 1:
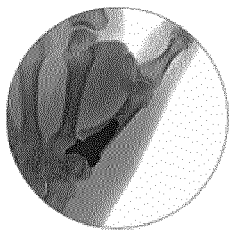
FIGS. 1 to 3 are images representative of the prior art, as discussed above.
Figure 2:
Figure 3:
Figure 5C:
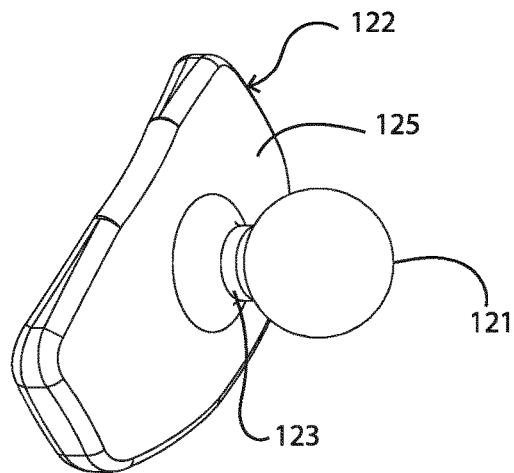
FIG. 5(c) is a perspective view of the proximal part.
Figure 6:
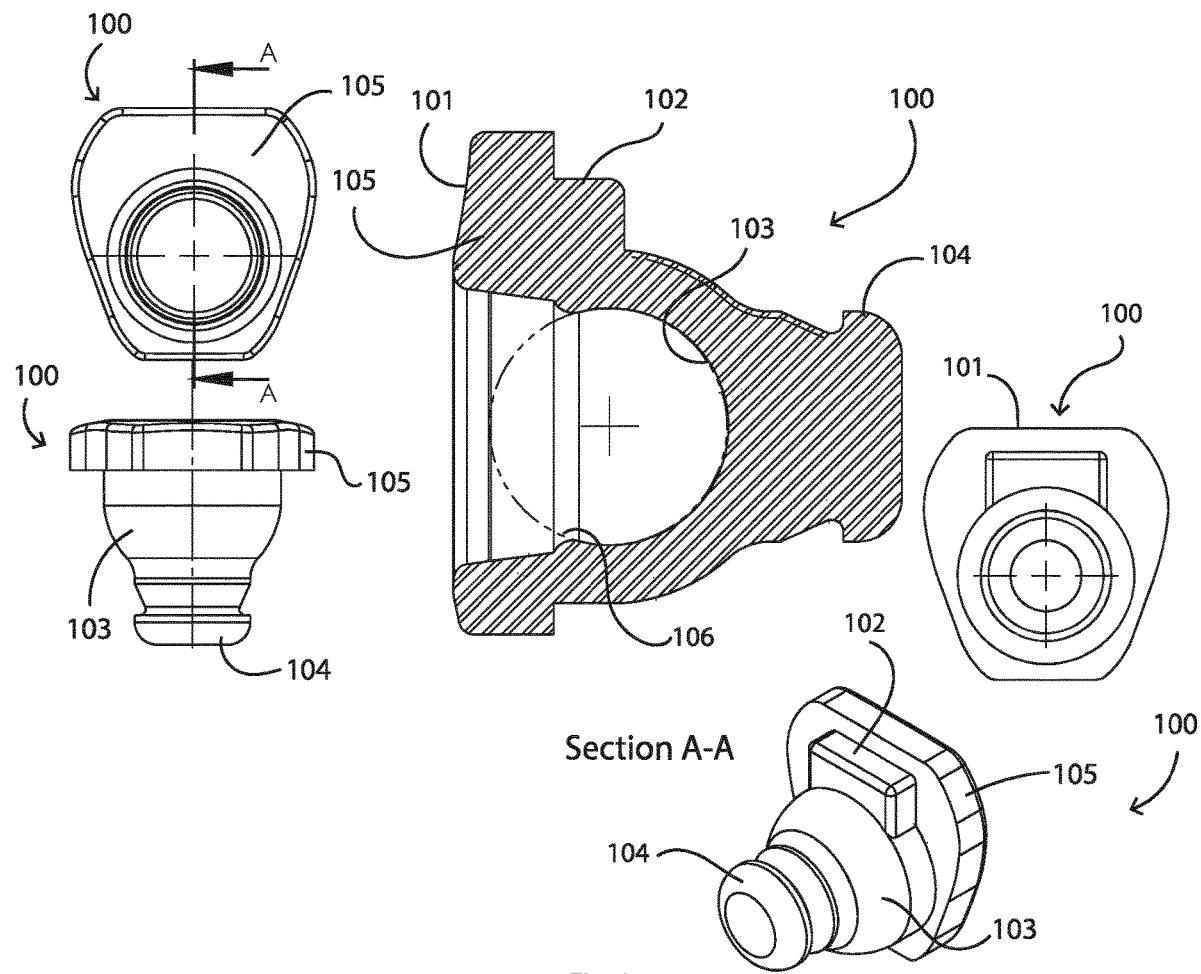
FIG. 6 is a set of views showing a portion of the coupling and distal part of the implant, particularly an insert in a stem of the distal part, including top plan, end, perspective, and cross-sectional views.

Referring to FIGS. 4 to 8 a hemi arthroplasty implant 1 has a distal part 110 for intramedullary engagement in the metacarpal, with an insert 100 in a stem 111, and a proximal part 120 for translational engagement over the trapezium. In this case the implant 1 is for a mammalian first carpometacarpal joint as shown in FIGS. 1 to 3 for spacing a trapezium bone of the joint from a first metacarpal bone of the joint while allowing translational movement of the first metacarpal bone in relation to the trapezium bone (which acts as an abutting platform). The distal part 110 is configured for intramedullary engagement with an end of the first metacarpal bone.

The proximal part 120 has a curved saddle-shaped platform 122 with a proximal-facing surface 124 for sliding on or traversing the trapezium bone, and a distally-facing surface 125 for abutting the flange 105. An articulating coupling comprises a neck 123 bridging the saddle 122 to a ball 121. This allows controlled articulation of the trapezium and first metacarpal bones. The implant is configured for multi-axial motion with translational movement over a bone in the proximal second part (120) and rotation of the distal part (110) about the articulating coupling (121, 103).

The implant 1 may be converted to a total arthroplasty implant because the second (proximal) part and the articulating coupling are removable in situ, and the first (distal) part comprises an engagement feature for engaging a replacement articulating coupling and a replacement part to replace the articulating coupling 123/121 and the second part 120 respectively. The replacement part is configured for implanting in bone. This conversion is described in detail below under the heading "Implant Conversion".

The insert 100 of the distal part 110 has a buffer interface feature, in this case a flange 105 with a contoured proximally-facing surface 101. Distally of this surface there is a shoulder (not shown) which acts as a key engaging a keyway in the stem 111 and preventing rotation of the insert 100 in the stem. The insert 100 forms a socket 103 with a rim 106 to receive the articulating coupling ball 121. There is snap-fit engagement of the ball 121 in the socket 103, behind the socket's rim 106, to enable the assembly of an articulating hemi-arthroplasty intra-operatively, and it may also prevent disassembly of the device in vivo. The socket can be central or offset in any direction or angle as needed.

Further distally, the insert 100 comprises an annular locking rim 104 for snap-fitting into a corresponding groove 116 of the stem 111 recess 115 which accommodates the insert 100. Engagement of the insert 100 into the stem 111 is effective due to the resilience of the insert material and the fact that there is comprehensive surface-to-surface contact in a snap-fitting manner between the rim 104 and its corresponding engagement surface within the stem 111. The insert is keyed by the shoulder 102 to prevent rotation and potential consequent back side wear.

The stem 111 socket 115 includes the annular groove 116 to allow snap-fitting of the rim 104 of the insert 100, and more distally it includes a female threaded blind hole 117.

The flange 105 (and in this case the whole insert 100) is of a resilient polymer material which is preferably a polymer, such as UHMWPE (in any of its forms, possibly including vitamin E) or PEEK, in any of its forms. It may alternatively be of other materials commonly used in orthopaedics such as Pyrocarbon (PyC), or ceramic depending on the wear patterns expected of the construct. The insert 100 is of a material which is different from the metal material of the articulated coupler ball 121 and neck 123, hence avoiding any Galvanic-type interactions which may cause excessive wear and/or chemical reactions which give rise to contaminants. Likewise, the (polymer) material of the insert is different from the metal material of the stem 111 for the same reasons. In general metal-to-metal contact interfaces are avoided in the implant. While a polymer material is good for wear, the biomechanical advantages of the flange i.e. breaking up the two axes of rotation, may be more important, and as such the flange could possibly be made of any suitable material. An example would be where the insert (or "liner") is made of a ceramic material, but the head is made of PEEK, which would still enable a snap fit engagement for the articulating coupling. It is generally preferred that the flange and the socket are not of a relatively hard material as that might not permit a snap fit for anything other than a material with low modulus/high resilience. This may be the other way around, for example, if the head is a polymer and the liner is a ceramic, the soft polymer material may still snap fit into the hard ceramics socket.

The flange material resilience is preferably sufficient to allow compression in use, to an extent desired to achieve gradual conversion of motion between the axes. For this implant, for the thumb, the thickness of the flange 105 is in preferably in the range of 0.5 mm to 4 mm, and preferably 1.0 mm to 3.0 mm. The implant may be provided as a kit in which there is the proximal part 122, the stem 111 of the distal part 110, and a range of two or more inserts each of which fits into the stem 111 but has a different flange thickness. The flange thickness sets the range of relative motion allowed, and in the example illustrated it is 40°. In general, the flange is preferably configured to provide a cone of motion in the range of 30° and 50° of the distal part about the proximal part. This allows the surgeon to choose the desired cone of motion. The implant thus achieves a predictable wear pattern. Also, decreasing the cone of motion reduces the chances of dislocation. It should be noted that for this type of joint, multi-axial, the full range of motion is actually about 80° when one takes into account the sliding motion of the proximal part over the trapezium bone.

Figure 7:
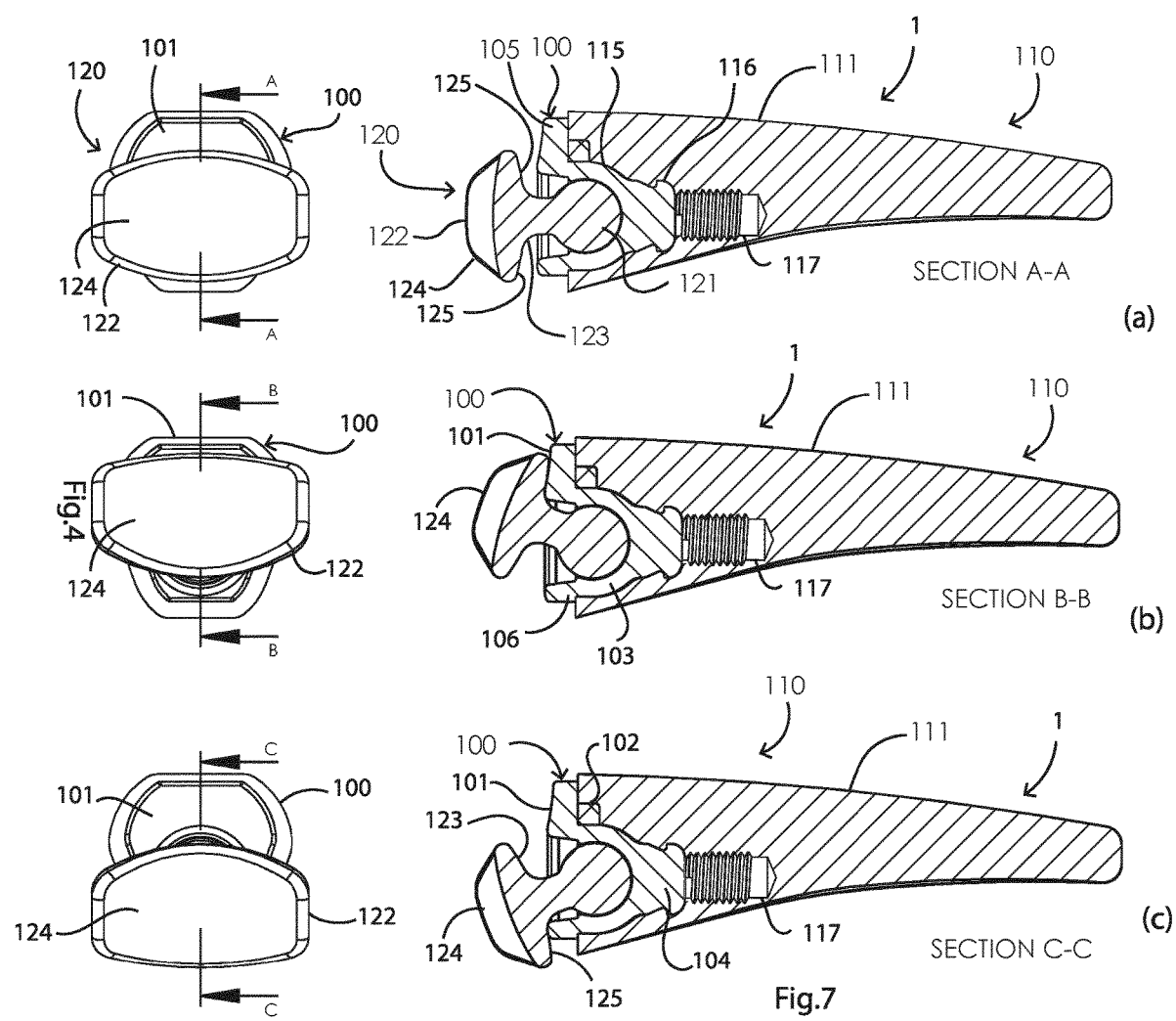

Moreover, the flange 105 contoured surface 101 is configured to match a corresponding mating distal surface 125 of the saddle 122, to cause the motion of forces between the two axes of motion to be limited in a step-wise manner. Hence, there is not an abrupt change in force, or "flip-flop" between the two axes. The mating surfaces 101 and 125 provide a large surface area for contact as illustrated in FIG. 7.

By having a load bearing surface 101 interposed between the axes, the forces are distributed in a more controlled, more natural, and more physiological manner. The relative motion around the articulated coupling is limited in one example to about 40°. This extent of motion is sufficient for use of the implant after deployment, but it also helps to ensure that there are not excessive impact forces between the surfaces and there is a smooth transition between the axes.

The liner snap-fit element 104 enables easy and effective assembly into the stem 111. Also, the liner snap-fit socket 103 facilitates the capture of a mating ball to form the ball-and-socket joint in a manner which is advantageous because of the resilience of the material of the insert 100. The flange 105 surface 101 is contoured to match the geometry of the head component to maximise surface contact and hence minimise liner wear.

The insert 100 is replaceable from within the stem i.e. it can be removed, and another inserted in its place in the case of excessive wear. The insert 100 advantageously limits the extent of relative rotation in the abduction-adduction and flexion-extension planes. As shown in FIG. 7 the saddle 122 has less freedom to rotate upwardly in this view and when contact is made with the surface insert 100 there is full-surface contact between the saddle 122 and the contoured surface 101. Preferably, the flange's contoured surface is tapered radially and distally and the saddle's corresponding mating surface is tapered radially and proximally.

On the lower side as viewed in FIG. 7, there is a smaller flange surface area, but the same effects and advantages apply. It will be appreciated that the insert 100 causes the impingement issue to be ameliorated.

Figure 9:
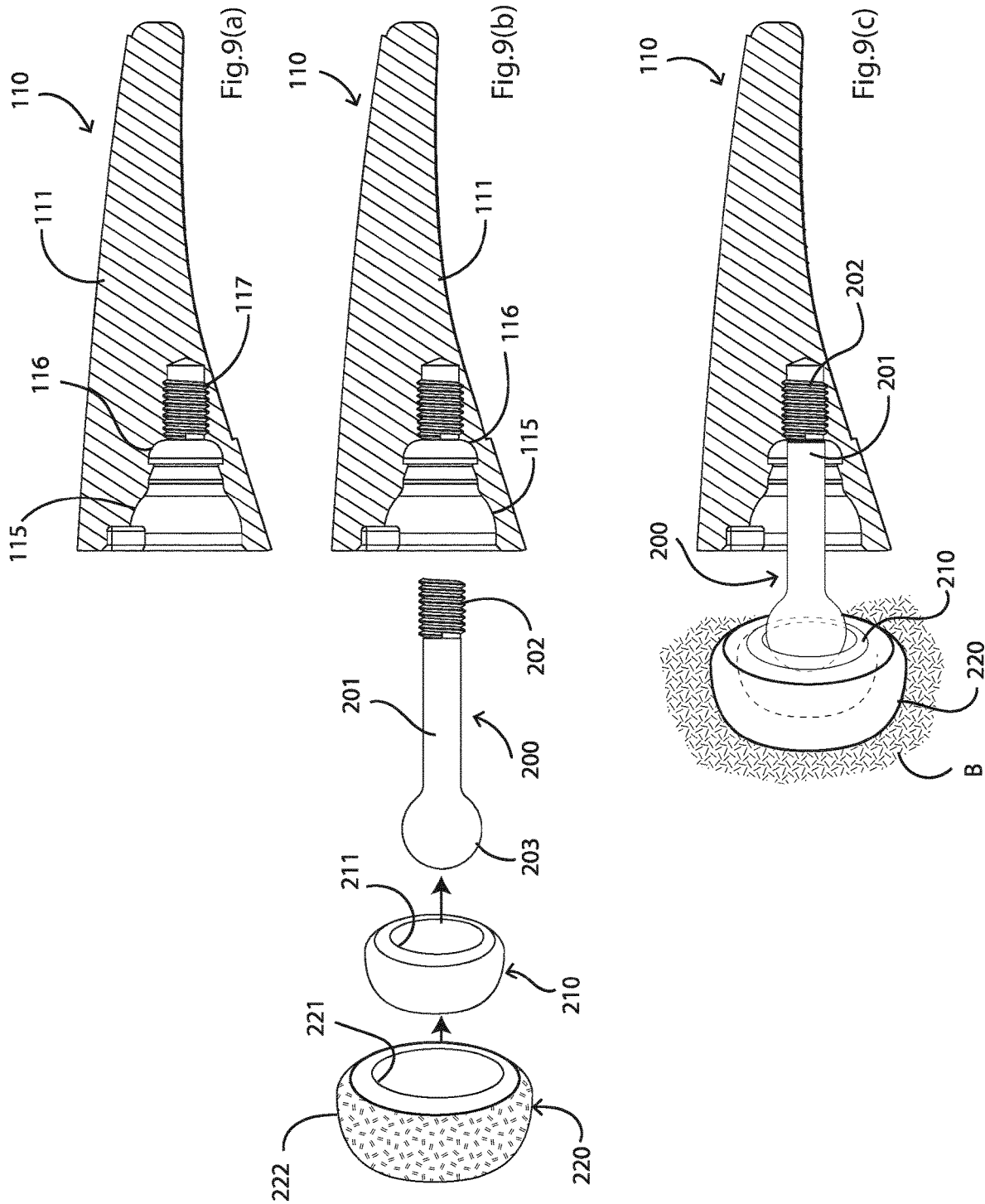

Implant Conversion (FIG. 9)

The implant 1 may be converted to a total arthroplasty implant in revision surgery, due for example to a changed clinical indication. This is achieved by providing a converter comprising a conversion or replacement second part which is implantable and a conversion or replacement coupling, either separately or as part of a kit including the implant 1.

The replacement coupling is indicated as 200, with a stem 201 having a threaded distal end 202 and a ball 203 at the proximal end.

The replacement part comprises a liner 210 in a trapezial cup 220. The ball 203 is configured to fit within the liner 210 having a socket 211 to receive the ball in a snap fit. The liner 210 is in turn configured to fit in the trapezial cup 220 having a socket 221 to receive the liner 210, and having an external roughened surface 222 for engaging bone at the proximal side of a joint.

In the case of a revision surgery with changing from a hemi arthroplasty to a total arthroplasty, the stem 111 of the implant 1 is left in situ. The second part 120 and the insert 100 are removed, exposing the threads 117 of the stem 111. The threads 117 are an engagement feature which is orientated for optimum location of the replacement coupling 200 for conversion of the implant to a total arthroplasty joint implant. The orientation and depth of the threaded socket 117 is optimal for the ball 203 to be positioned as described below.

The replacement coupler 200 is then threaded into place with the threaded end 202 of the stem 201 engaging the threaded socket 117. his causes the replacement coupling 200 to be fixed in place, anchored on the stem 111in a fixed and stable relationship. The replacement coupling 200 is mechanically akin to an extension of the stem. This provides the ball 203 at a fixed position proximally of the first part 110, the location of the ball 203 being optimal for articulation at this joint.

The surgeon may then prepare the trapezium bone and insert the replacement part 220 into the bone in a conventional manner. The trapezium bone had not been affected in the original surgery.

The liner 210 of the replacement part is inserted into the socket 221. This forms a ball-and socket articulation with the cup 220 and the liner 210 placed in the trapezium, and the ball 203 snap-fitted into the socket 211 of the liner 210. This is illustrated in FIG. 9(c).

In more detail, referring to FIG. 9:
a) Proximal part 120 (with the integral articulating coupling ball 121) and liner insert 100 (with the integral articulating coupling socket 103) are removed.
b) Replacement part and coupling are provided, including the trapezial cup 220, the liner 210, the head or coupler 200 with the ball 203 and the threads 202.
c) The threaded end 202 of the coupler 200 is engaged in the threaded socket 117 of the stem 111. The cup 220 is surgically implanted into a recess formed in the proximal bone B. This forms an assembled implant 110, 200, 210, 220 forming a total arthroplasty without a need for stem replacement. Advantageously, the hemi arthroplasty implant does not require remodelling or resection of the trapezium bone, all trapezium bone stock is in place for the placement of the trapezial cup element of the total arthroplasty implant.

In this way, the hemi arthroplasty implant can be successfully revised to a total arthroplasty using the modularity of components instead of significant surgical revision techniques to achieve this aim.

Also, the threads 117 can also function as a stem exchange mechanism in case the surgeon wants to alter the choice of stem intra-operatively. Moreover, the threads can function as a stem removal mechanism in case the surgeon wants to remove the stem 110 after some period to time for example to revise the procedure to a trapeziectomy operation or some variant of this procedure. Moreover, the threads 117 can be used for initial insertion of the stem 111 in the original surgery.

Referring to FIG. 10, an alternative implant includes the first part 110, the articulating coupling 123/121, and the second part 120 as described above. This drawing shows the implant after conversion to a total arthroplasty implant, in which the first part 110 remains, but the parts 120 and 123/121 are replaced by a replacement coupler comprising:

A stem 401 with a threaded end engaging the threaded socket 117.

An internal plug-shaped wider portion of the stem 404 which is integral with the stem 401 and is shaped to fit into the stem's socket 115. The stem wider portion 404 therefore has part of the same external configuration as the insert 100.

An integral nut 405 to allow convenient fastening of the threaded end 402 into the socket 117.

A ball 403 which is mounted by a neck 406 to be off-axis (in other embodiments it is on-axis or is off-axis in a different manner).

A total arthroplasty implant is completed by using the replacement part 210/220 as described above, engaging the ball 403. The extent and direction of the offset is chosen to suit the clinical need, and the depth of the threads are chosen so that with full tightening of the replacement coupler into the socket 117 the pre-determined ball orientation is achieved.

This arrangement may be regarded as having an "adaptive neck". By setting the thread length under the flange, the position of the neck and ball can be set in any predetermined position relative to the longitudinal axis of the stem when the hexagon 405 of the flange is secured to the base of the stem. Multiple offsets are determined by a range of such designs, each having a different angle of ball neck to hexagonal flange.

In other embodiments the threaded head of the coupler may have an element to lock it in place such as an additional thread design or secondary locking component.

The ball head may nominally be 4 mm or a variant of such depending on the design of the liner and socket of the trapezium components.

The trapezium cup may be coated, or have a surface finish, to enable optimal osteointegration or interference fit. The trapezial cup may be monopolar or bipolar i.e. single articulation or double articulation.

The invention is not limited to the embodiments described but may be varied in construction and detail. For example, the first part may have an engagement feature other than a threaded socket, such as a male threaded fastener component or a fastener component of any other type such as a push-fit fastener, possibly using a friction fit. The implant may be provided as a kit with multiple converters, preferably each of a different size, so that a choice is available to the surgeon.

Figure 11B:
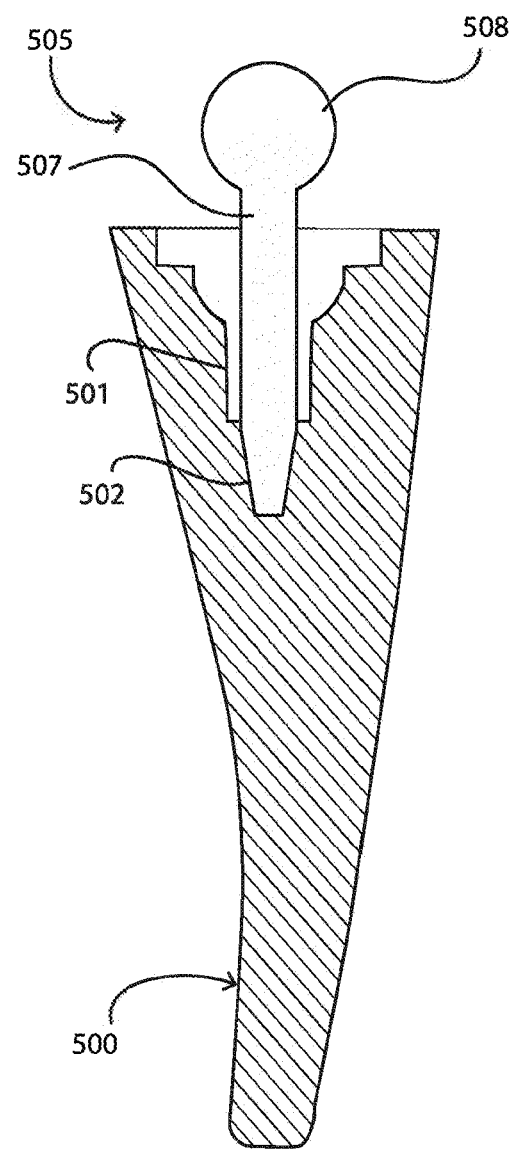

Referring to FIGS. 11(a) and 11(b) a first part has an intramedullary stem 500 for insertion into the first metacarpal. The stem 500 has a socket 501 with a female Morse taper 502 at its inner end. A replacement articulating coupling 505 comprises a distal end 506 with a male Morse taper shape corresponding to that of the female Morse taper 502. The coupling 505 has a stem 507 and a proximal ball 508 for connection of a replacement second part with a socket engaging the ball 508, such as the components 210 and 220.

Referring to FIGS. 12(a) and (b), a first part has an intramedullary stem 600 for insertion into the first metacarpal. The stem 600 has a socket 601 with a snap-fitting annular groove 602 at its inner end. A replacement articulating coupling 605 comprises a distal end 606 with an annular rim 609 corresponding to that of the groove 602. The coupling 605 has a stem 607 and a proximal ball 608 for connection of a replacement second part with a socket engaging the ball 508, such as the components 210 and 220. The stem 607 also has a shoulder rim 610 to provide stability for engagement of the replacement coupling 605 into the stem 600.

It is envisaged that any of the engagement features may be used in combination. For example, there may be a Morse taper in combination with a snap-fit feature and/or with a threaded engagement features.

Any of the components may be made of metal (examples include Titanium, or Colbalt Chrome), or Plastic (examples include UHMWPE or PEEK). In any combination i.e. a metal head/plastic stem, or plastic head/metal stem, a snap fit may be possible. This may function adequately where for example there is threads on the stem side, and a snap fit on the head if it is fabricated from a plastic material.

Also, the replacement cup may comprise a bipolar cup in which the ball rotates in an inner liner, which in turn can rotate in an outer liner, which in turn is itself fixed to a cup shell.

Also, the implant may be for a joint other than a mammalian first carpometacarpal joint, such as a hip, a shoulder, an elbow, a carpal/wrist, metatarsophalangeal, or ankle.

Also, the replacement coupling may be tilted without an enlarged portion, for example, akin to the replacement coupling 200 but with the stem 201 tilted off-axis with respect to the threaded end 202 to a desired extent.

The invention claimed is:

1. A hemi arthroplasty bone joint implant comprising:
a distal first part configured to be implanted into bone, the distal first part comprising an engagement feature,
a proximal second part configured to engage bone in a translational manner,
an articulating coupling between the distal first part and proximal second part, wherein the implant is configured for multi-axial motion with translational movement of the proximal second part over a bone and rotation of the distal first part about the articulating coupling, and
a converter comprising:
a replacement coupling for replacing the articulating coupling by engagement with the engagement feature, and
an implantable replacement second part,
wherein the replacement coupling is arranged to engage with the engagement feature of the distal first part and the replacement second part,
wherein the proximal second part and the articulating coupling are removable in situ during revision surgery.

2. The bone joint implant as claimed in claim 1, wherein the engagement feature comprises a bolt or threaded socket aligned for positioning of the replacement coupling for conversion to a total arthroplasty joint implant.

3. The bone joint implant as claimed in claim 2, wherein the engagement feature is a threaded socket and the threaded socket is at an angle relative to the distal first part for optimum positioning of the replacement coupling with respect to an axis of the distal first part.

4. The bone joint implant as claimed in claim 3, wherein the threaded socket opens into a socket in the distal first part, and a liner is removably insertable into the socket of the distal first part, wherein the threaded socket is exposed after removal of the proximal second part and articulating coupling.

5. The bone joint implant as claimed in claim 4, wherein the liner is configured to limit relative rotational motion about the articulating coupling, and to provide resilience for contact between the distal first part and proximal second part.

6. The bone joint implant as claimed in claim 5, wherein the liner comprises a flange extending radially and around at least a portion of the articulating coupling, and wherein the flange is of a material which is more resilient than a material which it contacts.

7. The bone joint implant as claimed in claim 6, wherein the flange has a contoured surface matching an abutting surface of the proximal second part upon articulation of the distal first part and proximal second part in use to extreme positions, and further wherein the distal first part has an intramedullary stem, and the contoured surface is spaced apart proximally from a proximal end of the intramedullary stem.

8. The bone joint implant as claimed in claim 7, wherein the contoured surface of the flange is annular.

9. The bone joint implant as claimed in claim 6, wherein the flange has a thickness ranging from 0.5 mm to 4.0 mm.

10. The bone joint implant as claimed in claim 9, wherein the flange has a thickness ranging from 1.0 mm to 3.0 mm.

11. The bone joint implant as claimed in claim 6, wherein the flange is of a material which is non-metal and is different from the material of a contacting surface.

12. The bone joint implant as claimed in claim 6, wherein the flange is configured to provide a cone of motion in the range of 30° to 50° of the distal first part about the proximal second part.

13. The bone joint implant as claimed in claim 6, wherein the articulating coupling is a ball-and-socket coupling and the liner includes the socket of the articulating coupling and a lock feature for snap-fitting into the distal first part.

14. The bone joint implant as claimed in claim 1, wherein the implant is for a mammalian first carpometacarpal joint, and the distal first part is configured for intramedullary engagement with an end of the first metacarpal bone and the proximal second part is configured for translational motion on the trapezium bone.

15. The bone joint implant as claimed in claim 1, wherein the engagement feature comprises a Morse taper male or female part and the replacement coupling comprises a corresponding engaging engagement feature.

16. The bone joint implant as claimed in claim 1, wherein the engagement feature comprises a snap-fitting part and the replacement coupling comprises a corresponding engaging engagement feature.

17. The bone joint implant as claimed in claim 1, wherein the replacement coupling comprises an enlarged portion to fit within a socket of the distal first part.

18. The bone joint implant as claimed in claim 1, wherein the replacement coupling comprises an integral nut for fastening the replacement coupling to the distal first part.

19. The bone joint implant as claimed in claim 1, wherein the replacement coupling comprises a neck supporting a ball which is tilted at an angle to a longitudinal axis of the coupling.

20. The bone joint implant as claimed in claim 19, wherein the replacement coupling has a threaded end for engaging the engagement feature of the distal first part, wherein an extent of rotation to a final position determines an angle of tilt of the neck and the ball.

21. The bone joint implant as claimed in claim 1, wherein the implantable replacement second part comprises a cup to receive a ball.

22. The bone joint implant as claimed in claim 21, wherein the implantable replacement second part further comprises a cup liner to directly receive a ball of the replacement coupling.

23. The bone joint implant as claimed in claim 1, wherein the distal first part comprises an intramedullary stem for implanting in a bone.

24. A method of converting a hemi arthroplasty bone joint implant of claim 1 to a total arthroplasty implant, the method comprising:
- removing the proximal second part and the articulating coupling, and
- implanting the replacement second part of the converter in a bone and connecting the replacement second part to the distal first part with the replacement coupling.

25. The method as claimed in claim 24, wherein the hemi arthroplasty bone joint implant is across a mammalian first carpometacarpal joint, with the proximal second part arranged for translational motion on the trapezium bone and the distal first part engaged within an end of the first metacarpal bone.

26. A kit comprising:
- a hemi arthroplasty bone joint implant, the implant comprising:
  - a distal first part configured to be implanted into bone, the distal first part comprising an engagement feature,
  - a proximal second part configured to engage bone in a translational manner, and
  - an articulating coupling between the distal first part and proximal second part, wherein the implant is configured for multi-axial motion with translational movement of the proximal second part over a bone and rotation of the distal first part about the articulating coupling; and
- a plurality of converters, each converter comprising:
  - a replacement coupling for replacing the articulating coupling by engagement with the engagement feature, and
  - an implantable replacement second part,
  - wherein the replacement coupling is arranged to engage with the engagement feature of the first part and the replacement second part.

27. The kit of claim 26, wherein the plurality of converters includes at least two converters, wherein the at least two converters are of different sizes.

* * * * *

UNITED STATES PATENT AND TRADEMARK OFFICE
CERTIFICATE OF CORRECTION

PATENT NO. : 12,138,173 B2
APPLICATION NO. : 17/442736
DATED : November 12, 2024
INVENTOR(S) : Filip Stockmans et al.

Page 1 of 1

It is certified that error appears in the above-identified patent and that said Letters Patent is hereby corrected as shown below:

On the Title Page

Column 2, Line 2 of the Abstract, Delete "tor" and insert --for--.

Page 2, Column 1, Line 2 of the Abstract, Delete "toral" and insert --total--.

Signed and Sealed this
Twenty-seventh Day of May, 2025

Coke Morgan Stewart
*Acting Director of the United States Patent and Trademark Office*